US00PP18696P2

(12) United States Plant Patent
Bradford

(10) Patent No.: US PP18,696 P2
(45) Date of Patent: Apr. 1, 2008

(54) NECTARINE TREE NAMED 'SNOW PEARL'

(50) Latin Name: *Prunus persica*
Varietal Denomination: Snow Pearl

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 11/637,897

(22) Filed: Dec. 13, 2006

(51) Int. Cl.
*A01H 5/00* (2006.01)

(52) U.S. Cl. ..... Plt./188
(58) Field of Classification Search ..... Plt./188, Plt./190
See application file for complete search history.

(56) References Cited

U.S. PATENT DOCUMENTS

PP7,507 P 4/1991 Bradford
PP7,918 P 7/1992 Bradford
PP11,695 P 12/2000 Bradford

*Primary Examiner*—Kent Bell

(57) ABSTRACT

The present invention relates to a new and distinct variety of nectarine tree, *Prunus persica,* broadly characterized by a medium size, vigorous, hardy, self-fertile, productive and regular bearing tree. The fruit matures under the ecological conditions described in late August, with first picking on Aug. 24, 2006. The fruit is uniformly large in size, sub-acidic and sweet in flavor, globose in shape, clingstone in type, firm in texture, white in flesh color, and almost full red with only slight freckling in skin color.

1 Drawing Sheet

Botanical classification: *Prunus persica.*
Variety denomination: 'SNOW PEARL'.

BACKGROUND OF THE VARIETY

In a continuing effort to improve the quality of shipping fruits, I, the inventor, typically hybridize a large number of peach, nectarine, plum, apricot, and cherry seedlings each year. The present invention relates to a new and distinct variety of nectarine tree, which has been denominated varietally as 'SNOW PEARL'. The present variety was hybridized by me in 1996, grown as a seedling on its own root in my greenhouse, and transplanted to a cultivated area of my experimental orchard located near Le Grand, Calif., in Merced County (San Joaquin Valley).

The variety was developed as a first generation cross using 'Ruby Diamond' (U.S. Plant Pat. No. 7,918) nectarine as the selected seed parent and 'Regal Pearl' (U.S. Plant Pat. No. 11,695) nectarine as the selected pollen parent. A single tree from the stated cross was selected as the claimed variety. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its selected seed parent, 'Ruby Diamond' nectarine, by producing fruit that is nearly globose in shape, and full red in skin color, but is distinguished therefrom by producing nectarines that are sub-acidic instead of acidic in flavor, that are white instead of yellow in flesh color, that are clingstone instead of freestone, and that mature about seven weeks later.

The present variety is most similar to its selected pollen parent, 'Regal Pearl' (U.S. Plant Pat. No. 11,695) nectarine, by producing nectarines that are nearly globose in shape, firm in texture, sub-acidic in flavor, and white in flesh color, but is distinguished therefrom by having a lower chilling requirement, by having globose instead of reniform leaf glands, by having a sweet instead of bitter kernel, and by producing nectarines that have much less skin freckling, that are somewhat larger in size, and that mature about one week later.

SUMMARY OF VARIETY

In summary, the present variety is characterized by a medium size, vigorous, hardy, self-fertile, productive and regular bearing tree. The fruit matures under the ecological conditions described in late August, with first picking on Aug. 24, 2006. The fruit is uniformly large in size, sub-acidic and sweet in flavor, globose in shape, clingstone in type, firm in texture, white in flesh color, and almost full red with very little freckling in skin color.

DRAWING

The accompanying photograph consists of four whole fruits positioned to display the characteristics of the skin color and form, one fruit divided transversely to the suture plane to reveal the flesh and stone, two insets to reveal buds and blossoms in various stages, and various leaves.

POMOLOGICAL CHARACTERISTICS

Referring now more specifically to the pomological characteristics of this new and distinct variety of nectarine tree, the following the been observed under the ecological conditions prevailing near Le Grand, Merced County (San Joaquin Valley), Calif. and was developed at the state of full ripe on Sep. 1, 2006, on the first multiplied tree during its fifth growing season. All major color code designations are by reference to the Inter-Society Colour Council, National Bureau of Standards. Common color names are also used occasionally.

TREE

Size: Medium, reaching and maintaining a height of 9' [2.74 m.] and a spread of 9' [2.74 m.] after five growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Spreading and dense.

Form: Vase formed.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning necessary.

Fertility: Self-fertile.

Bearing: Regular bearer with no alternate bearing yet observed.

Approximate chilling requirement: 625 hours.

Trunk:

*Size.*—Medium, reaching a maximum diameter of 3¾" [95 mm.] after the fifth growing season.

*Texture.*—Shaggy.

*Bark color.*—A Brownish gray [64. brGy] and Grayish reddish brown [46. gy.rBr] variegation.

*Lenticels.*—Approximately Number Per Square Inch: 8. Color: Moderate orange yellow [71. m.OY]. Typical Size: ⅛" [3.2 mm.] to 7/16" [11.1 mm.]. Shape: Eye-shaped to elongated.

Branches:

*Size.*—Diameter of limb is 2" [51 mm.] measured 12" above the crotch. 1¼" [32 mm.] measured 12" above the first fork.

*Texture.*—Smooth on first and second year wood, increasing roughness with age.

*Color.*—1st Year Wood Topside: Grayish red [19. gy.R]. 1st Year Wood Underside: Brilliant yellow green [116. brill.YG]. Older Wood: Deep yellowish brown [75. deep yBr].

*Lenticels.*—Number Per Square Inch: More than 40 on second year wood. Color: Light yelllowish brown [76.1 l.yBr]. Typical size: 1/32" [0.8 mm.] to 3/32" [2.4 mm.] on second year wood. Shape: Elongated.

Leaves:

*Size.*—Medium. Average Length: 5¼" [133 mm.]. Average Width: 1 9/16" [40 mm.].

*Arrangement.*—Alternate.

*Thickness.*—Medium.

*Form.*—Elliptical.

*Apex.*—Acuminate.

*Base.*—Acute, with a base angle of 75 to 85 degrees.

*Surface.*—Smooth.

*Color.*—Doral Surface: Moderate olive green [125. m.OlG]. Ventral Surface: Moderate yellow green [120. m.YG].

*Margin.*—Finely serrate.

*Venation.*—Pinnately net veined.

*Vein color.*—Pale yellow green [121. p.YG].

*Petiole.*—Average Length: ½" [12.7 mm.]. Average Thickness: 1/16" [1.6 mm.]. Color: Light yellow green [119. l.YG].

*Stipules.*—Number: 2 per leaf, up to 6 per growing tip. Average Length: 7/16" [11.1 mm.]. Color: Brilliant yellow green [116. brill.YG]. becoming Moderate brown [58. m.Br] with maturity.

*Glands.*—Number: 2 to 4 per leaf. Position: Both alternate and opposite pairs observed with the first two usually positioned on petiole and the rest on the base of blade. Size: Medium. Form: Globose. Color: Light yellow green [119. l.YG] becoming Grayish brown [61. gy.Br] with age.

*Leaf buds.*—Pointed, medium in size.

Flower buds:

*Hardiness.*—Hardy, with respect to central California winters.

*Diameter.*—Typically ⅜" [9.5 mm.] 1 week before bloom.

*Length.*—Typically 11/16" [17.5 mm.] 1 week before bloom.

*Form.*—Not appressed.

*Surface.*—Pubescent.

*Color.*—Light purplish pink [249. l.pPk].

Flowers: Perfect, complete, perigynous, usually a single pistil, typically thirty or more stamens, five sepal and petal locations alternately positioned.

*Type.*—Showy, very large.

*Average flower diameter.*—1⅞" [47.6 mm.].

*Number of petals.*—Usually five, extra petal fragments and double blossoms occasionally observed.

*Petal shape.*—Circular to oval.

*Petal margin.*—Somewhat wavy.

*Average petal diameter.*—¾" [19.1 mm.].

*Average petal length.*—13/16" [20.6 mm.].

*Petal apex.*—Rounded.

*Petal base.*—Rounded to somewhat truncate.

*Petal color.*—Pale pink [7. p.Pk] toward the apex, Light pink [4. l.Pk] toward the base.

*Anther color.*—Moderate red [15. m.R] over a Light yellow [86. l.Y] center at bloom onset.

*Stigma color.*—Light greenish yellow [101. l.gY].

*Sepal color.*—Dark purplish red [259. d.pR].

*Sepal length.*—¼" [6.4 mm.].

*Sepal width.*—7/32" [5.6 mm.].

*Average pistil length.*—13/16" [20.6 mm.].

*Average stamen length.*—⅝ [15.9 mm.].

*Fragrance.*—Moderate.

*Blooming period.*—Medium, three days after 'Spring Bright' (U.S. Plant Pat. No. 7,507) nectarine.

*Onset of bloom.*—One percent on Feb. 27, 2006.

*Date of full bloom.*—Mar. 10, 2006.

*Duration of bloom.*—One to two weeks, dependent on ambient temperature.

*Number per cluster.*—1 to 3 with single flowers most common.

FRUIT

Maturity when described: Full ripe, Sep. 1, 2006.

Date of first picking: Aug. 24, 2006.

Date of last picking: Sep. 4, 2006.

Size: Uniform, large.

*Average diameter axially.*—2¾" [70 mm.].

*Average diameter across suture plane.*—2 15/16" [75 mm.].

*Average diameter across cheek plane.*—2¾" [70 mm.].

*Typical weight.*—7.2 ounces [204 grams].

Form: Uniform, globose, slightly asymmetrical.

*Longitudinal section form.*—Round to elliptical.

*Axial view.*—Round with a hump on one side of the suture.

Suture: A shallow groove near the base, a shallow trough along the side, and a sharp groove toward the apex, ending just beyond the pistil point with a slight depression.
Ventral surface: Rounded, lipped stronger toward the apex.
Lips: Unequal.
Cavity: Flaring, circular to elongated in the suture plane, suture usually showing on one side, Yellowish white [92. yWhite] stem markings present.
*Depth.*—⅝" [15.9 mm.].
*Breadth.*—1⅛" [28.6 mm.].
Base: Truncate.
Apex: Rounded.
Pistil Point: Apical, negligible in length, depressed within the suture.
Stem: Medium.
*Average length.*—⅜" [9.5 mm.].
*Average width.*—3/16" [4.8 mm.].
Skin:
*Thickness.*—Medium.
*Surface.*—Smooth.
*Tenacity.*—Tenacious to flesh.
*Astringency.*—Non-astringent.
*Tendency to crack.*—None observed in dry season.
*Color.*—Very deep red [14. v.deep R] mottled over a Dark Pink [6. d.Pk] background with a slight amount of Moderate orange [53. m.O] freckling toward the apex.
Flesh:
*Color.*—Yellowish white [92. yWhite] with Moderate red [15. m.R] streaking next to the stone.
*Surface of pit cavity.*—Very deep red [14. v.deep R] broken fibers when twisted from stone.
*Amygdalin.*—Scarce.
*Juice.*—Abundant, rich.
*Texture.*—Firm, meaty, melting.
*Fibers.*—Abundant, fine.
*Ripens.*—Slightly earlier at the apex.
*Flavor.*—Sub-acidic and very sweet, typically 18 brix.
*Aroma.*—Slight.
*Eating Quality.*—Excellent.

STONE

Type: Clingstone.
Form: Oval.
Hilum: Narrow.
Base: Straight.
Apex: Acute with an average angle of 85 degrees and a 1/16" [1.6 mm.] tip.
Sides: Equal.
Surface: Irregularly furrowed toward the apex, pitted toward the base.
Ridges: Jagged.
External color: Dark brown [59. d.Br].
Pit wall color when cracked: Moderate brown [58. m.Br].
Cavity surface color: Strong brown [55. s.Br].
Average pit wall thickness: ¼" [6.4 mm.]
Average width: 1½" [38.1 mm.].
Average length: 1 3/16" [30.2 mm.].
Average breadth: ⅞" [22.2 mm.].
Tendency to split: Slight.
Kernel:
*Form.*—Oval.
*Skin color.*—Brownish orange [54. brO] when dry.
*Pellicle color.*—Grayish brown [61. gy.Br].
*Vein color.*—Greyish brown [61. gy.Br].
*Taste.*—Sweet.
*Viable.*—Yes.
*Average width.*—½" [12.7 mm.].
*Average length.*—⅞" [22.2 mm.].
*Amygdalin.*—Scarce.

USE

Market: Fresh market and long distance shipping.
Keeping quality: Good, fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is most similar to its selected pollen parent, 'Regal Pearl' (U.S. Plant Pat. No. 11,695) nectarine, by producing nectarines that are nearly globose in shape, firm in texture, sub-acidic in flavor, and white in flesh color, but is distinguished therefrom by having a lower chilling requirement, by having globose instead of reniform leaf glands, by having a sweet instead of bitter kernel, and by producing nectarines that have much less skin freckling, that are somewhat larger in size, and that mature about one week later.

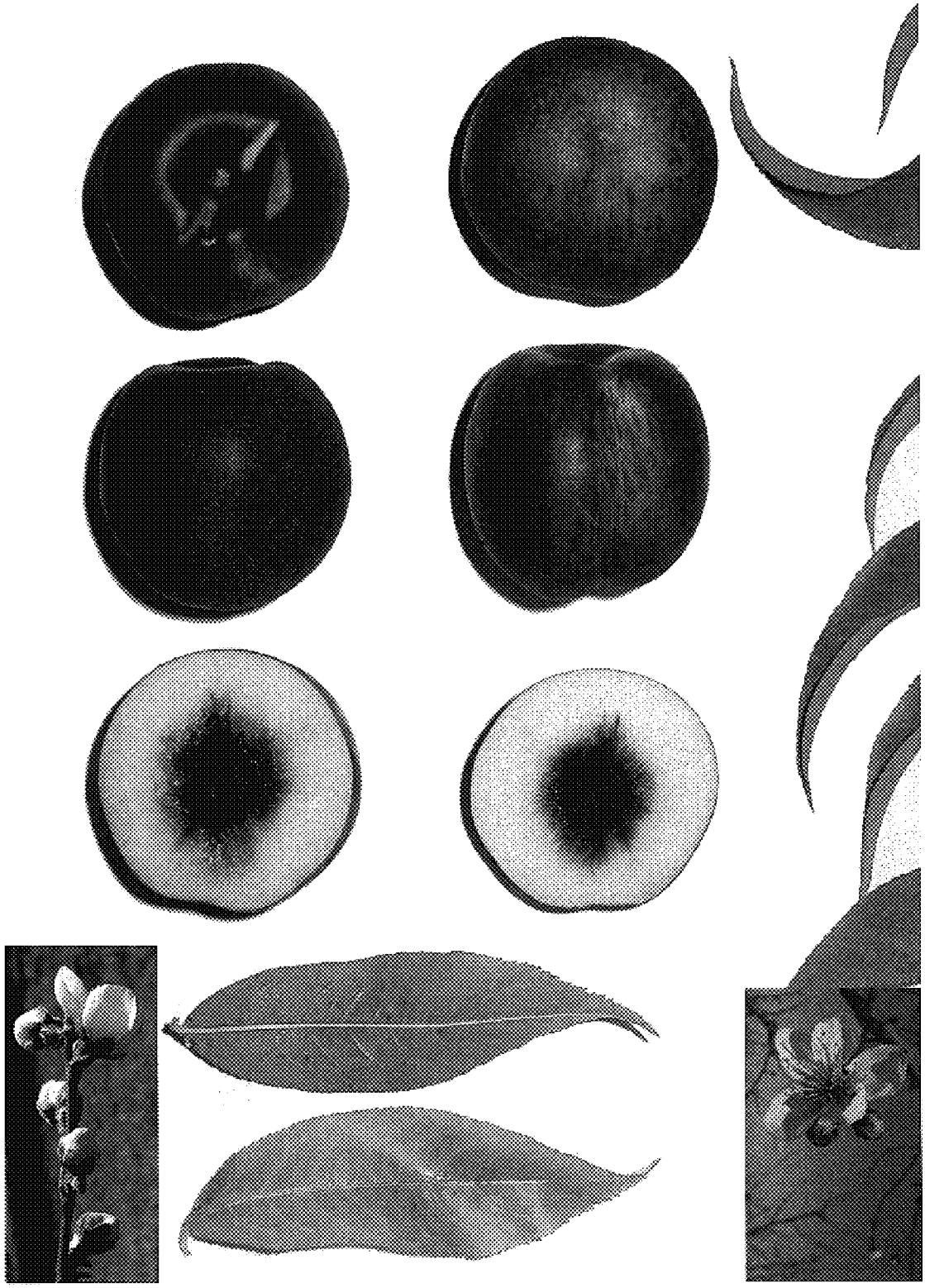

* * * * *